United States Patent [19]

McAleer et al.

[11] 4,088,748

[45] May 9, 1978

[54] HEPATITIS B SURFACE ANTIGEN

[75] Inventors: William J. McAleer, Ambler; Edward H. Wasmuth, Telford, both of Pa.

[73] Assignee: Merck & Co., Inc., Rahway, N.J.

[21] Appl. No.: 793,662

[22] Filed: May 4, 1977

Related U.S. Application Data

[63] Continuation-in-part of Ser. No. 737,931, Nov. 2, 1976, abandoned.

[51] Int. Cl.$^2$ ........................ A61K 39/12; C12K 7/00

[52] U.S. Cl. ........................................ 424/89; 195/1.5

[58] Field of Search ............................ 424/89; 195/1.5

[56] References Cited

PUBLICATIONS

Dreesman et al., J. of Virology, vol. 16, No. 3, Sep. 1975, pp. 508 & 509.

Harris–Techniques in Experimental Virology (1964) pp. 156 and 159.

*Primary Examiner*—Sam Rosen

*Attorney, Agent, or Firm*—Donald J. Perrella; Julian S. Levitt

[57] ABSTRACT

Biological fluid containing hepatitis B surface antigen is concentrated using ammonium sulfate, and subjected to an isopycnic banding followed by rate zonal banding.

11 Claims, No Drawings

HEPATITIS B SURFACE ANTIGEN

RELATED APPLICATION

This application is a continuation-in-part of copending application Ser. No. 737,931 filed Nov. 2, 1976, now abandoned.

BACKGROUND OF THE INVENTION

1. Field of the Invention

This invention relates to hepatitis B surface antigen particles ($HB_sAg$) and, more particularly, to a process for preparing $HB_sAg$ in high yield and purity.

Hepatitis B is one of the types of viral hepatitis which results in a systemic infection with the principal pathologic changes occuring in the liver. This disease affects mainly adults and is maintained chiefly by transfer of infection from long term carriers of the virus. Usual methods of spread are by blood transfusion, contaminated needles and syringes, through skin breached by cuts or scratches, by unsterilized dental instruments as well as by saliva, veneral contact or exposure to aerosolized infected blood.

The incubation period of type B hepatitis is relatively long: from 6 weeks to 6 months may elapse between infection and the onset of clinical symptoms. The illness usually begins with fatique and anorexia, sometimes accompanied by myalgia and abdominal discomfort. Later jaundice, dark urine, light stools and tender hepatomegaly may appear. In some cases, the onset may be rapid, with appearance of jaundice early in association with fever, chills and leukocytosis. In other cases jaundice may never be recognized and the patient may be aware of a "flu-like" illness. It is estimated that the majority of hepatitis infections result in a mild, anicteric illness.

2. Background of the Invention

Serum obtained from patients with hepatitis B infections contains three distinct morphologic forms which share a common surface antigen ($HB_sAg$) and which can be aggregated with specific antibody directed against $HB_sAg$. The largest of these morphologic forms, a 42-nm to 45-nm double shelled spherical particle, often referred to as the Dane particle (HBV), is believed to be the virus of hepatitis B. The outer surface or envelope of the Dane particle is the $HB_sAg$ particle which surrounds a 27-nm inner core which does not react with antibody against $HB_sAg$ and which contains a distinct antigen, the core antigen ($HB_cAg$). $HB_sAg$ can be used as an immunizing antigen against hepatitis B.

3. Objects of the Invention

It is, accordingly, an object of the present invention to provide an improved method for obtaining $HB_sAg$ particles. Another object is to provide a faster and more economical method for concentrating and purifying $HB_sAg$ particles. These and other objects of the present invention will be apparent from the following description.

SUMMARY OF THE INVENTION

Human biological fluid containing $HB_sAg$ is concentrated using ammonium sulfate and subjected to an isopycnic banding followed by a rate zonal banding.

DETAILED DESCRIPTION

The starting material for the purified $HB_sAg$ of the present invention is fluid containing $HB_sAg$. The fluid may be any human biological fluid containing $HB_sAg$ such as, for example, plasma, saliva, fecal extracts, nasal pharyngeal secretions, bile, spinal fluid, sweat, urine, semen, vaginal secretions, or menstrual blood. The plasma is obtained in conventional manner, e.g., by plasmaphoresis. The level of $HB_sAg$ in the human biological fluid may be measured in known manner by any suitable means, e.g., reversed passive hemagglutination or complement fixation. When the biological fluid is plasma, it may be treated directly or cooled and the cryoprecipitate which forms may be removed by light centrifugation, or $CaCl_2$ may be added to remove fibrinogen and clarified. The resulting fluid is treated with ammonium sulfate and the $HB_sAg$ in the resulting fluid is isolated by an isopycnic banding step followed by a rate zonal banding step.

In isopycnic banding the partially purified concentrate is contacted with a liquid medium having a density gradient therein which includes the density of the specific antigen being isolated. The liquid medium is then subjected to ultracentrifugation to attain an equilibrium distribution of the serum components through the density gradient according to their individual densities. Successive fractions of the medium are displaced and those containing the desired antigen, i.e. the fractions having a density of from about 1.21 to about 1.24 g/cc, are separated. The application of this technique to the purification of $HB_sAg$ is described in German specification 2,049,515 and U.S. Pat. No. 3,636,191. The concentrations of the solutions forming the gradient are selected so as to encompass the density range of from about 1.0 to about 1.41 g/cc. The liquid medium may be employed in the form of a linear gradient or a step gradient. Preferably it is employed in the form of a step gradient due to its inherent higher capacity for fractionation.

In rate zonal banding the partially purified concentrate is subjected to ultracentrifugation in contact with a liquid medium having a density gradient therein, but this time using the rate zonal technique i.e., at a rate and for a period such that equilibrium is not attained, the $HB_sAg$ and other residual serum components being distributed through the medium according to their sedimentation coefficients in the medium. The concentrations of the solutions forming the step gradient are selected so as to encompass the density range of from about 1.0 to about 1.28 g/cc. The rate zonal step is carried out until the $HB_sAg$ resides in the 1.13 to 1.16 density region. At this point the $HB_sAg$ is separated from the bulk of the crude plasma proteins and, most significantly, is also separated from the macroglobulin complement of the plasma. If the rate zonal step is carried out such that the desired $HB_sAg$ antigen reaches its equilibrium position, i.e., about 1.18 to about 1.20 g/cc, it has been found that a plasma macroglobulin fraction will appear as a contaminant in the desired $HB_sAg$ antigen fraction.

The liquid media used in the isopycnic banding step may be any density gradient in the appropriate ranges. Prior art solutes for such solutions include, e.g. sucrose, potassium bromide, cesium chloride, potassium tartrate and the like.

The isopycnic banding step is conveniently carried out in a centrifuge, for example, Electronucleonics-K, by filling the stationary rotor with saline solution, then successively displacing the saline solution upwards with aliquots of a liquid medium solution of increasing density until a step gradient is formed. The plasma is introduced at the top of the rotor displacing some of the highest density solution from the bottom. Typically, the volume of plasma is from about 15% to about 40% that of the step gradient. The centrifuge is brought up to speed through a programmed speed control system which prevents mixing during the initial reorientation phase. When equilibrium is attained and the product is in its proper density position, the rotor is slowed down through the same system to prevent mixing upon reorientation to the original configuration. Then the gradient is drained from below and the proper density cut collected. A similar technique is used in the rate zonal banding. The proper density cut from the rate zonal banding is the desired concentrate of hepatitis B antigen.

Due to the small size of $HB_sAg$, approximately 20 nm, the isopycnic banding step is quite time consuming, requiring about 18 hours of centrifuging. As a result, even operating 24 hours a day, 7 days a week, it is possible to process only about 4 batches per centrifuge per week. Productivity can be increased, of course, by utilizing additional centrifuges. This involves a tremendous capital investment, however, as each centrifuge is very expensive.

It has now been found that substantial increases in productivity and substantially reduced operating costs are obtained by treating the human biological fluid with ammonium sulfate before subjecting the fluid to isopycnic banding conditions. The amount of ammonium sulfate used should be at least about that amount sufficient to precipitate substantially all of the $HB_sAg$ in the fluid while avoiding precipitation of additional undesired proteinaceous matter. As a result of this precipitation, the $HB_sAg$ from several liters of fluid can be subjected to isopycnic banding in one batch whereas without ammonium sulfate precipitation, only a much smaller quantity of fluid can be subjected to isopycnic banding in a single batch. Generally, when the biological fluid is plasma from about 200 to about 250 g of ammonium sulfate are used per liter of plasma, and preferably about 225 g per liter of plasma. Lesser amounts do not precipitate all of the $HB_sAg$ while greater amounts precipitate additional undesired proteinaceous matter. When the fluid is plasma, with ammonium sulfate precipitation, the $HB_sAg$ in about 20 liters can be subjected to isopycnic banding in one batch; without ammonium sulfate precipitation only about 1.5 liters of plasma can be subjected to isopycnic banding.

After the ammonium sulfate is added, the fluid is agitated to help dissolve the ammonium sulfate. Preferably the fluid is agitated for at least about 3 hours at lowered temperature of from about 0° to about 10° C, preferably at about 5° C, and preferably at least about 4 hours. Additional agitation beyond about 4 hours is not harmful. The precipitate which forms is collected by centrifugation and the pellets resuspended in saline and dialyzed against saline to remove the ammonium sulfate. The resulting fluid concentrate is then subjected to an isopycnic banding using a gradient material having a permissable density range of from about 1.1 to about 1.4 g/cc.

The product from the isopycnic banding is dialyzed against PBS to remove the gradient material if it is dialyzable.

The product is then subjected to a rate zonal banding until the $HB_sAg$ is in the density range of from about 1.13 to about 1.16 g/cc. Any gradient material that yields this density range and is dialyzable and physiologically acceptable may be used. Typically this banding takes from about 16 to about 20 hours, preferably from about 17 to about 18 hours at about 30,000 rpm. At higher speeds less time is required, and at lower speeds more time is required.

According to a preferred aspect of the present invention the gradient is formed of sodium bromide. In contrast to heretofore used materials sodium bromide has definite advantages. The solubility of sodium bromide allows the use of high density solutions in the formation of gradients at refrigerator temperatures (2°–6° C). There are definite economic advantages to using sodium bromide over a salt such as cesium chloride as well as not having to contend with the problem of human toxicity from residual and $HB_sAg$ bound cesium ions. In sodium bromide gradient any ions bound to the $HB_sAg$ due to biophysical characteristics, will be sodium ions which are very compatible with the human biological system and do not present any toxicity problems.

The superior solubility of NaBr at lowered temperatures with respect to KBr permits the use of lowered temperatures more conducive to stability of biological materials. The use of a step gradient rather than a linear gradient is preferred as it accumulates impurities at the step boundaries and permits processing a larger volume of plasma in a single gradient.

The following example illustrates the present invention without, however, limiting the same thereto.

EXAMPLE

20 Liters of clarified plasma from hepatitis B donors are filtered through a 293 mm filter containing an AP 20 filter membrane (Millipore). Ammonium sulfate, 4.53 kg, is added to the filtrate which is then agitated gently overnight at 5° C. The precipitate which forms is collected by batch centrifugation at 7000 × g for 30 minutes using the JA-10 rotor (3 liter capacity per batch). The pellets post centrifugation are suspended in about 2.25 liters of saline. The concentrated suspension is then dialyzed against 40 liters of saline to remove the ammonium sulfate.

The rotor of a centrifuge, Electronucleonics K, is filled with 8,400 ml of phosphate buffer. After running the rotor up to 10,000 rpm to degas the system, the following step gradient is pumped into the bottom of the stationary rotor:

1. 2,000 ml of 10% NaBr, $\rho = 1.08$
2. 1,000 ml of 20% NaBr, $\rho = 1.17$
3. 1,500 ml of 30% NaBr, $\rho = 1.28$
4. 3,900 ml of 40% NaBr, $\rho = 1.41$ The dialyzed suspension containing $HB_sAg$, 2,250 ml, is pumped into the top of the stationary rotor displacing 2,250 ml of 40% NaBr from the bottom of the rotor. The rotor is accelerated to 30,000 rpm and run at this speed for 18 hours. After stopping the rotor 2,000 ml of $HB_sAg$ rich material in the 1.21 - 1.24 density region is collected and dialyzed against phosphate buffer.

The rotor is then filled with phosphate buffer, degassed as above, and the following step gradient pumped into the bottom of the stationary rotor:

1. 2,000 ml of 5% sucrose, $\rho - 1.02$
2. 1,650 ml of 15% sucrose, $\rho - 1.06$
3. 1,750 ml of 25% sucrose, $\rho = 1.10$ 4. 3,000 ml of 50% sucrose, $\rho = 1.23$ The $HB_sAg$ rich material from the NaBr isopycnic banding step 2,000 ml is pumped into the rotor top displacing 2,000 ml of 50% sucrose out the rotor bottom. The rotor is then run at 28,000 rpm for 18 hours. After stopping the rotor, 1,000 ml of $HB_sAg$ rich material in the 1.135 - 1.165 density region is collected.

What is claimed is:

1. A process for obtaining $HB_sAg$ from human biological fluid obtained from human hepatitis B donors comprising treating the fluid with sufficient ammonium sulfate to precipitate an antigen fraction comprising $HB_sAg$, subjecting the precipitated fraction to an isopycnic banding and to a rate zonal banding, and recovering $HB_sAg$ in the density range of from about 1.13 to about 1.16 g/cc.

2. A process according to claim 1 wherein the amount of ammonium sulfate is sufficient to precipitate substantially all of the $HB_sAg$ in the fluid but insufficient to precipitate a substantial amount of additional proteinaceous matter.

3. A process according to claim 1 wherein the fluid is plasma.

4. A process according to claim 3 wherein the amount of ammonium sulfate is up to about 250 g per liter of plasma.

5. A process according to claim 3 wherein the amount of ammonium sulfate is from about 200 to about 250 g per liter of plasma.

6. A process according to claim 3 wherein the amount of ammonium sulfate is about 225 g per liter of plasma.

7. A process according to claim 1 wherein after addition of ammonium sulfate, the fluid is agitated at from about 0° to about 10° C for at least about 3 hours.

8. A process according to claim 1 wherein after addition of ammonium sulfate, the fluid is agitated at from about 0° to about 10° C for at least about 4 hours.

9. A process according to claim 7 wherein the agitation is carried out at about 5° C.

10. A process according to claim 1 wherein the isopycnic banding gradient is NaBr.

11. A process according to claim 1 wherein the rate zonal banding gradient is sucrose.

* * * * *